United States Patent [19]

Zinnamosca et al.

[11] Patent Number: 5,559,031
[45] Date of Patent: Sep. 24, 1996

[54] APPARATUS FOR THE CONTINUOUS PRODUCTION OF ETHANOL FROM CEREALS

[75] Inventors: Francesco Zinnamosca; Massimo Berruti, both of Rome, Italy

[73] Assignee: Technipetrol S.p.A., Rome, Italy

[21] Appl. No.: 269,634

[22] Filed: Jul. 1, 1994

Related U.S. Application Data

[60] Continuation of Ser. No. 879,601, May 7, 1992, abandoned, which is a division of Ser. No. 353,641, Apr. 11, 1989, abandoned.

[30] Foreign Application Priority Data

Apr. 11, 1989 [IT] Italy ........................... 48298/87

[51] Int. Cl.$^6$ .................................................. C12M 1/40
[52] U.S. Cl. .......................... 435/289.1; 435/294.1; 435/308.1; 435/819
[58] Field of Search ........................ 435/161, 162, 435/163, 165, 287, 311, 316, 813, 819, 289.1, 291.1, 294.1, 308.1; 426/11, 13, 14; 99/276

[56] References Cited

U.S. PATENT DOCUMENTS

| | | | |
|---|---|---|---|
| 4,202,777 | 5/1980 | Schall | 210/405 |
| 4,287,303 | 9/1981 | Dahlberg et al. | 435/162 |
| 4,326,036 | 4/1982 | Hayes | 435/162 |
| 4,361,651 | 11/1982 | Keim | 435/161 |
| 4,366,322 | 12/1982 | Raymond | 549/489 |
| 4,419,448 | 12/1983 | Kretz | 435/161 |
| 4,425,433 | 1/1984 | Neves | 435/161 |
| 4,460,687 | 7/1984 | Ehnstrom | 435/162 |
| 4,810,647 | 3/1989 | Monceaux et al. | 435/161 |

FOREIGN PATENT DOCUMENTS

| | | | |
|---|---|---|---|
| 0049994 | 4/1982 | European Pat. Off. | 435/161 |
| 2442887 | 8/1980 | France | 435/161 |
| 0152890 | 9/1982 | Japan | 435/161 |
| 0152891 | 9/1982 | Japan | 435/161 |

*Primary Examiner*—William H. Beisner
*Attorney, Agent, or Firm*—Thomas R. Vigil

[57] ABSTRACT

The abstract is used to process cereals to obtain ethanol. In the apparatus, a limpid phase of a slurry with water and hydrolyzed starch is supplied to a saccharification stage and an output of the saccharification stage is supplied to a fermentation stage to obtain a fermentation product and a wine from the fermentation product is supplied to a distillation stage to obtain ethanol. A stationary screen with a mesh of between 150 and 300 microns is positioned in the apparatus for receiving at an input of the screen, the slurry with water and hydrolyzed starch. The stationary screen has a turbid overscreen outlet and a limpid outlet containing a limpid solution having particles up to 150–300 microns. The limpid outlet is coupled to the saccharification stage so as to supply the limpid solution to the saccharification stage. A vacuum band filter has an inlet coupled to the turbid overscreen outlet from the stationary screen. The vacuum band filter has a turbid filter outlet which is coupled back to the input to the stationary screen and has an outlet for a filtration panel. A mechanical squeezing filter is coupled to the filtration panel outlet from the vacuum band filter, has a turbid filter outlet that is coupled to the inlet of stationary screen and has a dehydrated panel outlet.

9 Claims, 5 Drawing Sheets

APPARATUS FOR THE CONTINUOUS PRODUCTION OF ETHANOL FROM CEREALS

CROSS REFERENCE TO RELATED APPLICATIONS

This application is a continuation of U.S. application Ser. No. 07/879,601, filed May 7, 1992, now abandoned, which is a division of U.S. application Ser. No. 07/353,641, filed Apr. 11, 1989, now abandoned.

BACKGROUND OF THE INVENTION

This invention relates to a process for the production of ethanol from cereals wherein the fermentation is continuously carried out with clean musts, i.e. with sugar solutions provided by enzyme saccharification from an acidified hydrolyzed product of cereals from which the insoluble solids have been separated by filtration.

The invention relates also to a continuous cycle apparatus to carry out said process.

The ethanol is provided both in a synthetic way from ethylene and by fermentation from sugar solutions. Due to the increase of ethylene cost the production of alcohols by fermentation has assumed a greater importance and industrial interest.

The fermentation is carried out under anaerobic conditions and with a non-continuous process or, which is less usual, with a continuous process by using sugar solutions with an usual concentration of fermentable sugars of about 15% in weight so as to provide maximum concentrations of 8–10% in volume once the sugars are consumed.

When the transformation of sugars into alcohols is completed, the wine is usually centrifugated to separate the yeast and is led to a distillation apparatus for the recovery of the alcohol.

The separation of the yeast cannot be carried out when turbid solutions are treated.

The yeast is recycled to the fermentation unit of the continuous fermentation plants.

The waste waters, i.e. the residue from the distillation of the fermented alcohol must have a high pollution load so that a preliminary treatment is necessary before their wasting.

The most commonly used treatment consists of a concentration by evaporation in a multiple-effect system until a concentration of about 60% of solid content is reached; the concentrated residues from the distillation of the fermented alcohol musts have a good bargain as fodder but a high vapour quantity is requested for their concentration.

The starting materials for the production of ethanol in a fermentative way can be sugar substances like sugar cane or sugarbeet molasses, sugar cane, sugarbeet, sugar sorghum and fruit, starchy substances like cereal, cassava and potatoes or finally cellulose substances like agricultural residues, wood and urban waste.

In Europe and the United States the trend in the last years is to provide ethanol from the surplus cereal production and from molasses; in tropical countries and first of all in Brazil the most used starting material is the sugar cane or the molasses.

The present status of art provides knowledges and applications on a sound basis as far as the continuous fermentation of clean solutions mainly deriving from sugar starting materials is concerned, while as for the production of ethanol from cereals (maize, corn, sorghum, a.s.o.) the use of non-continuous fermentation system is commonly provided without preliminary separation of the solid content, thus giving rise to the following disadvantages:

1. very long fermentation times (72 hours or more);
2. impossibility of separating and recycling the yeast with the consequence of a low efficiency;
3. operative difficulties in fermentation units of large dimensions due to the presence of solids suspended in the must;
4. problems of eliminating the must in the fractionating columns still due to the presence of high percentages of suspended solids;
5. high energy consumption and mechanical problems in drying the residue material.

The reason for such a situation is bound to the present state of the industry of producing ethanol from cereals, the aim of which has always been the production of alcoholic drinks without dealing, except for the recent times, with the problems relative to the production of ethanol in large quantities with both thermic and transforming efficiency.

A process (Biostill by Alfa-Laval) providing the continuous fermentation of concentrated sugar substrates and using as starting material molasses, cane, syrup and cereals has been thrown on the market in recent times.

Such a process causes the fermentation of a concentrated sugar solution provided, in case of cereals, by hydrolysis and saccharification of the starch and containing in suspension all insoluble solids present in the starting material.

In order to cause the starch to be separated, the fibers and the other insoluble solids are eliminated from the fermented wine by means of a stationary screen; the so clarified wine is then led to the centrifugal separator of the yeast.

The yeast is recycled for the continuous fermentation thereof and the limpid wine is led to the upper section of a stripping column for eliminating the ethanol (from the upper part); the exhausted wine is led back to the fermentation unit.

The insoluble solids separated from the screen are also led to the stripping column for the recovery of the residual ethanol.

The continuous transfer of the fermented wine to the stripping column, thus eliminating the ethanol, allows the fermentation to be continued with concentrated substrates, even if the content of ethanol is lower than 8% in volume in the fermentation unit; too high concentration of ethanol prevents the yeast to be active.

The residues from the distillation of the fermented alcohol musts outflowing from the bottom of the stripping column and containing all non-fermentable soluble solids and the insoluble substances are led directly to the drying system.

The Biostill process, however, has the following disadvantages:

1. The fermentation of solutions containing solid suspensions has structural and operative problems due to the necessity of maintaining an uniform stirring in the fermentation unit itself in order to prevent solids from being deposited;
2. The fermentation of concentrated sugar substrates requires the use of particular cultures of yeasts of the Saccharomyces type;
3. The obtained residues from the distillation of the fermented alcohol musts cannot be concentrated in a multiple-effect evaporation system due to the high concentration of insoluble solids and are then dried with a low thermal efficiency;
4. The treatment of dirty wine in the stripping column has non-negligible dirt problems.

This invention seeks to avoid all above mentioned problems by providing a process for the production of ethanol from integral cereals wherein the continuous fermentation take place on clean saccharified musts, i.e. (not concentrated) sugar solutions obtained by enzyme saccharification of an acidified hydrolyzed product obtained by an enzyme treatment of cereals meal after having separated by filtration the insoluble solids contained in said hydrolyzed product.

This is possible according to the invention with a process comprising the steps of:

- screening a hydrolyzed product obtained by an enzyme treatment of a cereal meal, thus providing a limpid phase and a turbid phase;
- filtering by washing in a horizontal band filter under vacuum the turbid phase, thus providing a filtration panel and a filtrate;
- subjecting the filtration panel to a further mechanical squeezing, thus providing a dehydrated panel and a filtrate;
- leading the turbid filtrates obtained in the filtration phases to the stationary screen, thus providing a limpid filtrate;
- subjecting the limpid filtrate and the limpid hydrolyzed product to the enzyme saccharification treatment, thus providing a solution of fermentable sugars;
- fermenting the sugar solution in a set of atmospheric fermentation units with outer cooling and recycling system;
- centrifugating the wine obtained from the fermentation, separating the microorganism and leading them to the first fermentation unit after acidification, thus providing a limpid alcohol solution which is the final product to be treated in the distillation unit.

The following advantages are achieved from such a process:

1. The separation of the insoluble solids before the fermentation phase allows the knowledge about the continuous fermentation with recycle of the yeast to be applied to clean musts (molasses, cane syrup, a.s.o.).
2. The continuous fermentation of clean musts requires reduced fermentation times of the order of 30—35 hours due to the increase of concentration of the microorganisms by the recycle of the yeast;
3. The fermentation of clean solutions at the usual sugar concentrations of 13–15% in weight allows commercial yeast to be used without need of preparing particular cultures;
4. The recycle of the yeast further allows the fermentation yield to be increased, thus avoiding to produce huge quantities of yeast at the beginning of any fermentation and during the same;
5. The elimination of suspended solids before of the fermentation allows the construction of fermentation systems of large dimensions to be simplified, and to make easier the operation thereof;
6. The distillation column for clean wines is not affected with problems of dirt causing frequently stops for maintenance;
7. The obtained residues from the distillation of the fermentated alcohol musts are free from insoluble solids and can be then concentrated in a multiple-effect evaporation system until a concentration of 60% in solid content is reached, thus achieving a strong energy saving with respect to a drying system. The filtering panels provided in the separation phase of the insoluble solids and destined for the zootechnic use are dehydrated by means of mechanical compression in order to reduce the consumption of vapour for the drying process.

It should be noted that there are other industrial applications providing the separation of the suspended solids from the saccharified must and the subsequent continuous fermentation with the drawback that the separation should be carried out at not so very high temperatures (about 60° C.) and in the presence of fermentable sugars.

According to the present invention the suspended solids are separated at high temperatures (about 85° C.) and in the presence of non-fermentable dextrines, thus reducing the danger of infection by microorganisms and making the separation easier due to the high temperature.

The invention will be better understood from the following description together with the annexed drawing showing only by way of non-limitative example a preferred embodiment of the invention.

DESCRIPTION OF THE PREFERRED EMBODIMENTS

Figure 1:
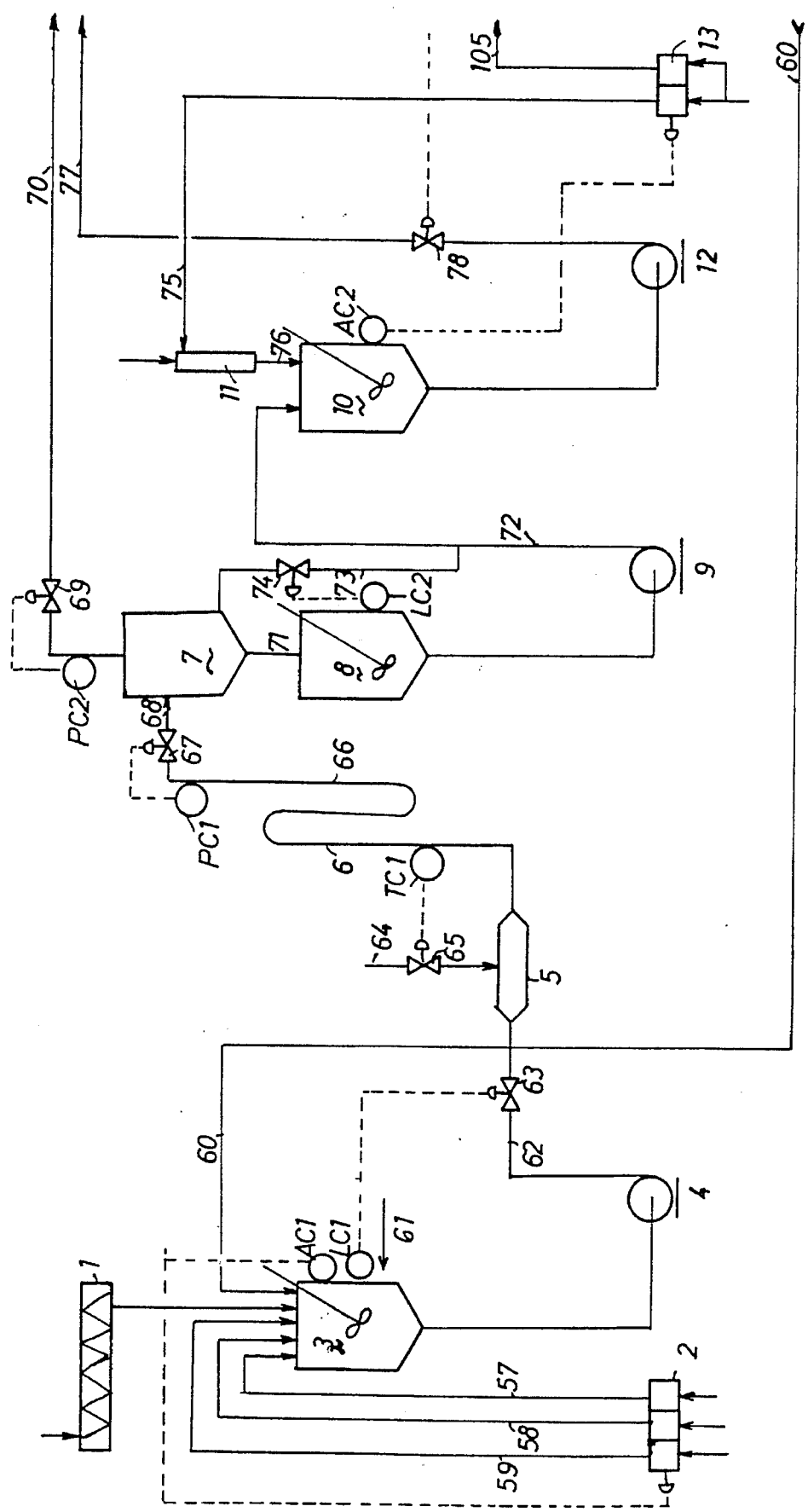
FIGS. 1, 2, 3, 4 combined together show schematically a preferred embodiment of the apparatus of this invention.
Figure 2:
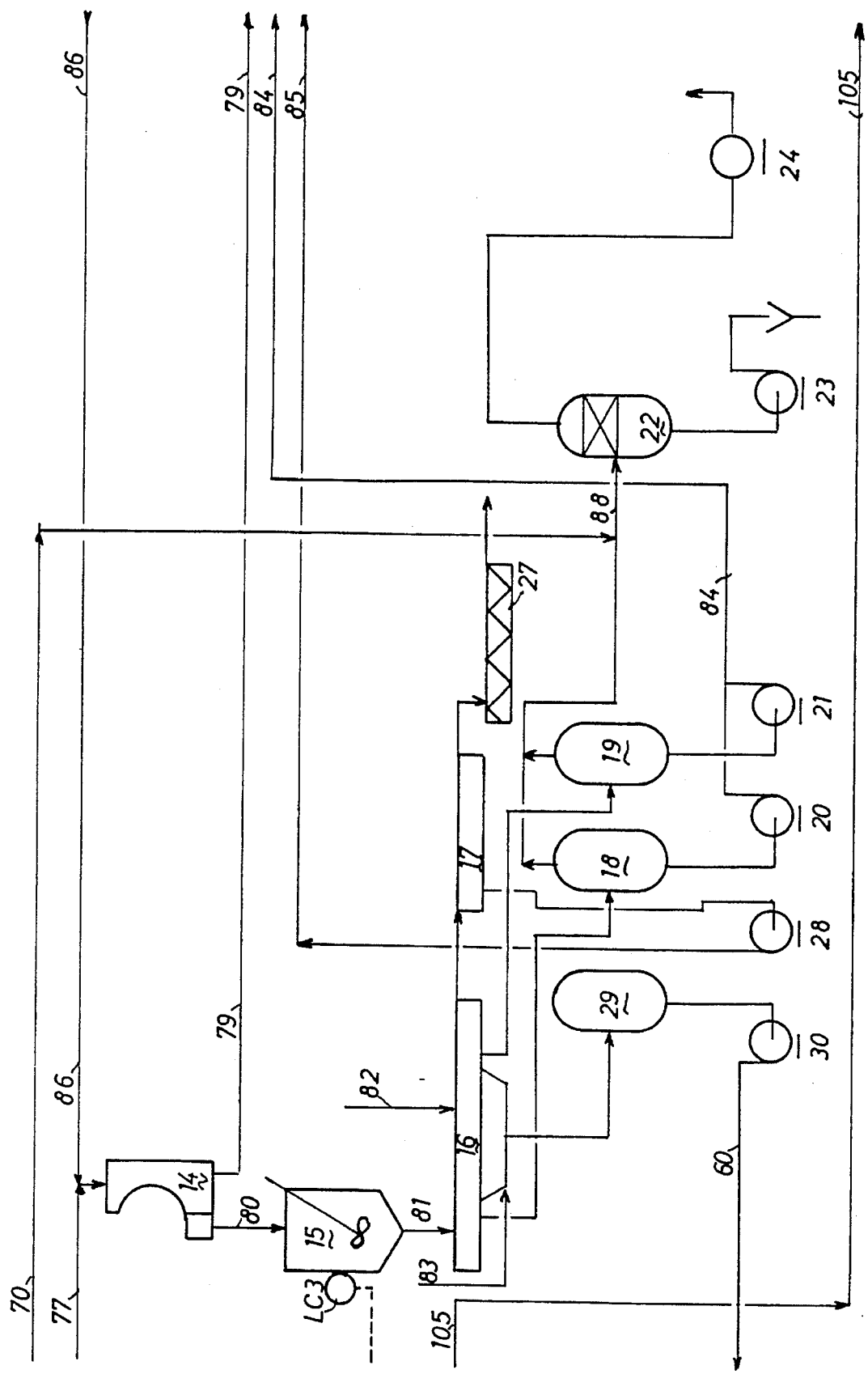
Figure 3:
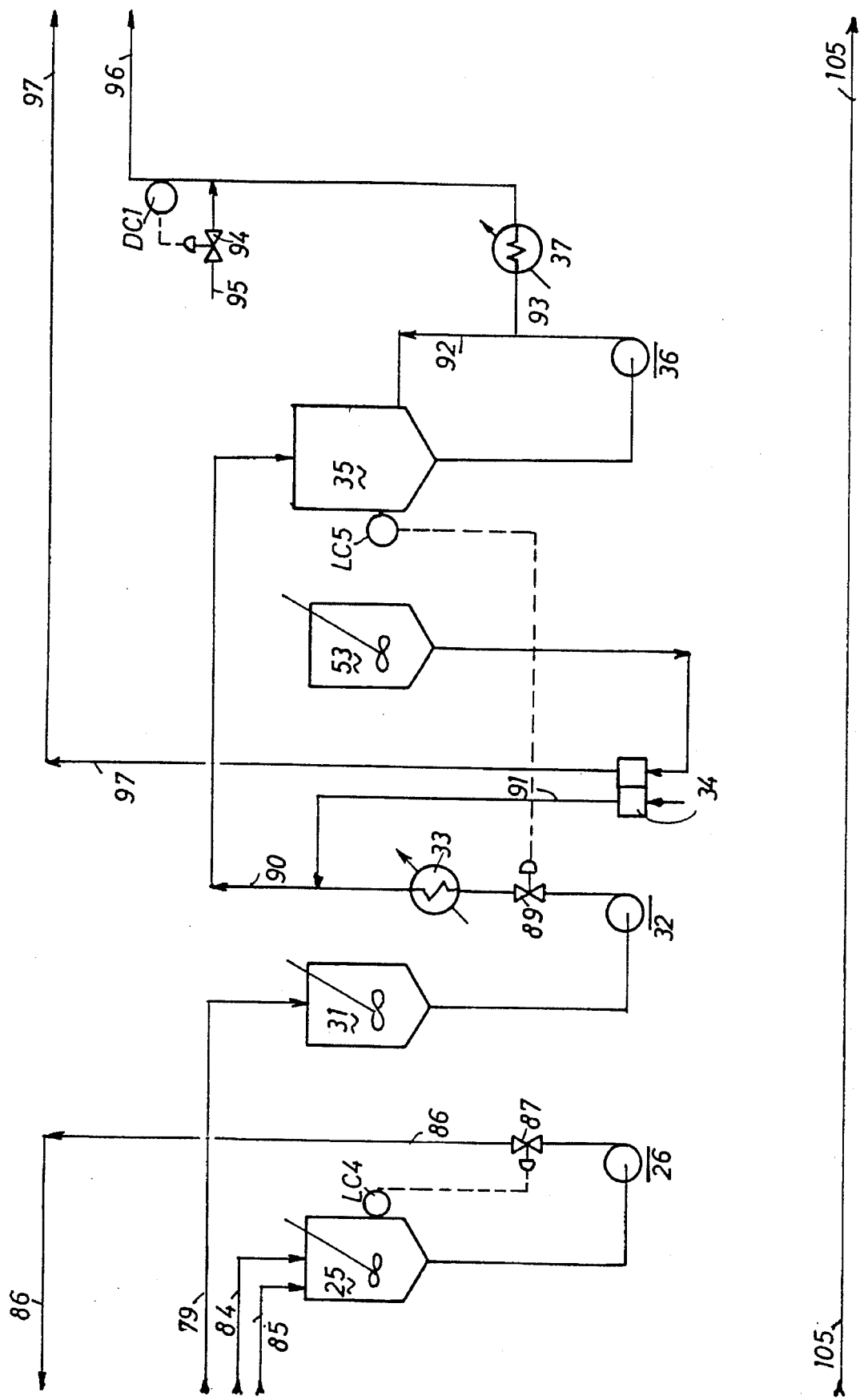
Figure 4:
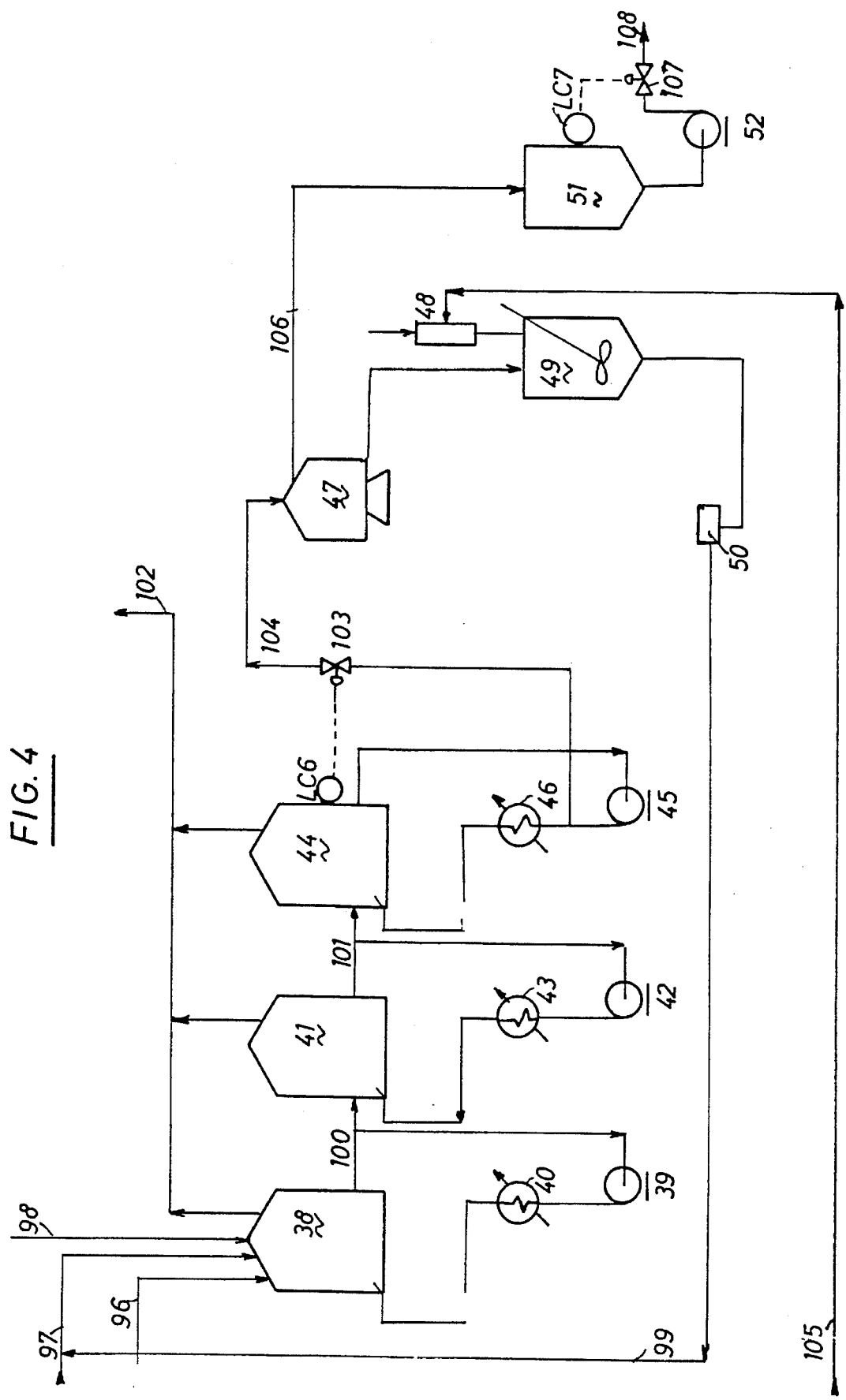
Figure 5:
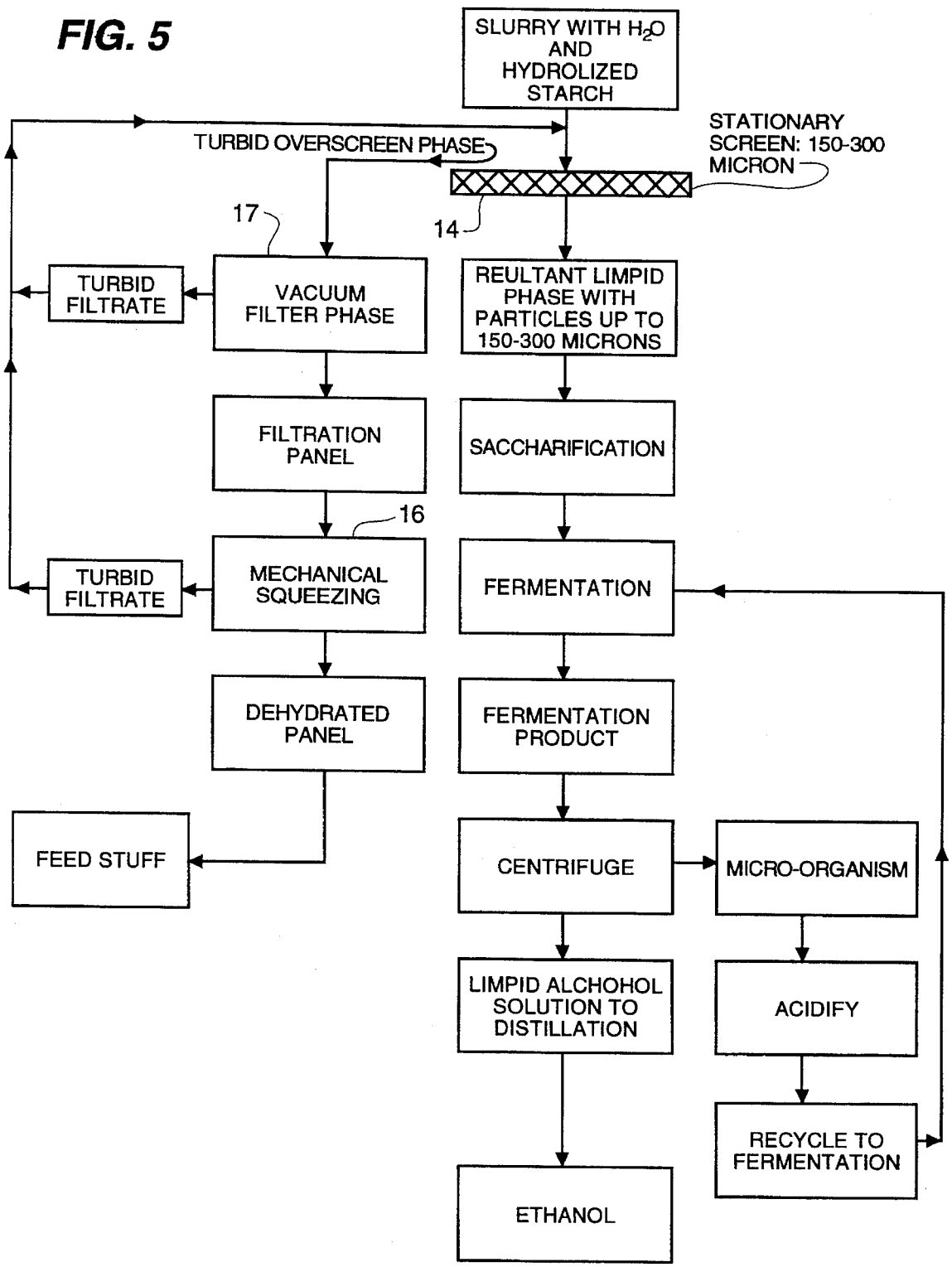
FIG. 5 is a block fluid flow diagram of the steps of the process carried out by the apparatus shown in FIGS. 1–4.

With reference to FIGS. 1,2,3 and 4, screw conveyer 1 introduces the cereal meal into vessel 3 in which the meal is in suspension and to which four lines 57, 48, 59, 60 are led. The rate of the cereal meal introduction is controlled by varying the speed of the screw conveyer.

Dilution water is added to suspension vessel 3 through line 60, soda solution through line 59, calcium chloride solution through line 58 and alpha-amylase enzyme solution through line 57: said organic substances are preportioned by three-head pump 2. The pH of the suspension is automatically regulated by controller AC1 acting on the capacity of the corresponding head of pump 2. The suspension is held by means of a mechanical stirrer and is heated directly by low pressure vapour introduced through line 61.

The meal suspension is led by pump 4 to the starch boiling system through line 62 and control valve 63 responsive to level controller LC1 for vessel 3.

The starch boiling and liquefaction system begins at vapour injector 5 in which the meal suspension is heated directly with middle pressure under control of temperature controller TC1 acting on valve 65 regulating the vapour introduced through line 64.

The suspension is then led through line 66 to conduit 66 assuring the necessary holding time at the requested temperature. The suspension is then expanded through control valve 67 actuated by pressure controller PC1 and is led through line 68 to expansion cyclone 7 operating under vacuum. The vacuum in cyclone 7 is automatically controlled by control valve 69 actuated by pressure controller PC2 which holds the requested vacuum condition by conveying the expansion vapour to the vacuum system through line 70.

The meal suspension is then led through conduit 71 to liquefaction vessel 8, in which by mechanical stirring the starch liquefaction phase is completed.

Feed pump 9 delivers a part of the hydrolyzed product to the following acidification phase through line 72; a great quantity of hydrolyzed product is also recycled to the bottom of expansion vessel 7 through line 73 to prevent by centrifugal action solids to be deposited. The recycled quantity is controlled by maintaining the level in vessel 8 constant by means of controller LC2 acting on valve 74.

The hydrolyzed product is acidified in vessel 10 with stirring by adding sulphuric acid pumped by two-head proportioning pump 13.

The concentrated acid is led through line 75 to stationary mixer 11 where it is diluted with water and then through line 76 it reaches acidification vessel 10.

The proportion of acid is automatically controlled by controller AC2 acting on the capacity of the corresponding head of pump 13.

The suspension of the acidified hydrolyzed product is pumped by pump 12 to the separation system for the suspended solids.

The solids separation system consists of stationary curved grid screen 14 which is supplied with the hydrolyzed product through line 77; the screen is also supplied with a recycled turbid filtrate (line 86) provided in the subsequent filtration phase. The interstices between the bars of the screen grid can be about 150–300 microns (100–50 mesh).

The screen separates a limpid phase, which is led to the following saccharification process through line 79, from a phase containing most of the solids in suspension which is led through line 80 to vessel 15 with mechanical stirrer which supplies the filtration system comprising filters 16 and 17 for the recovery of non-fermentable sugars as well as for the thickening of the insoluble solids.

The level of vessel 15 is automatically controlled by controller LC3 acting on control valve 78 located in the delivery line of pump 12 in order to assure a constant liquid head supplied to filter 16.

Filter 16 is supplied through line 81 with the concentrated suspension. Filter 16 is of the horizontal band type under vacuum and is provided with a warm water washing system 82 for the panel and with a cold water washing system 83 for the belts and cloths.

The belt and cloth washing water is recovered by vessel 29 and conveyed by pump 30 through line 60 to vessel 3 of the suspended meal for the necessary dilution, thus minimizing the consumption of water and the waste.

The filtration panel is led to a mechanical squeezing filter 17 in order to obtain the maximum dehydration thereof.

The dehydrated panel containing the solids, which are included in the meal and cannot be solubilized by the enzyme treatment (mainly insoluble fibers and proteins), is discharged from the filter by means of conveyer 27 and led to the final drying phase, if requested.

The filtrated liquids obtained in vacuum filter 16 are collected in vessels 18 and 19 under vacuum and pumped by pumps 20 and 21 to a filtrate collection vessel 25 through line 84.

The filtrate obtained in squeezing filter 17 is led by pump 28 through line 85 to the same vessel 25.

The turbid filtrate collected in vessel 25 is recycled by pump 26 to screen 14 through line 86 for the elimination of the still included solids; the level of vessel 25 is maintained constant by the controller LC4 acting on control valve 87.

In order to attain the requested vacuum in filter 16 and cyclone 7, the stems and vapours which cannot be condensed are led through lines 88 and 70, respectively, to mixture condenser 22 where the stem is condensed; the vapours which cannot be condensed are ejected to the atmosphere by vacuum pump 24 of the liquid ring type.

Water and vapours condensed in condenser 22 are drained by pump 23.

The clarified hydrolyzed product of screen 14 is led to the following clarification phase through line 79. Store vessel 31 is provided for the clarified production which is led by pump 32 through line 90 to a cooling plate exchanger 33 in order to bring the hydrolyzed product to the optimum saccharification temperature. The cooled solution reaches the saccharification tank 35 through line 90; the solution of the saccharification enzyme (amidoglycosidase) is injected in the line by the two-head proportioning pump 34 through line 91.

The saccharification takes place partially in presaccharification tank 35 and partially in the following fermentation tanks.

Presaccharification tank 35 is provided with a stirring system comprising a circulating pump 36 and mixing nozzle; the level is maintained constant by controller LC5 acting on control valve 89 regulating the rate of hydrolyzed product.

Pump 36 transfer the must to the fermentation phase through line 93 and allows tank 35 to be stirred through recycle line 92.

Before the must is led to the fermentation phase, it is cooled in plate cooler 37 and brought to the optimum dilution by an injection of water from line 95. The proportioning is automatically carried out by means of a density controller DC1 acting on control valve 94.

Under the requested conditions of dilution and temperature the must is led to the first of the continuous fermentation units 38 through line 96; the first fermentation unit is also supplied with a motor yeast cream through line 98, which is used only at the beginning of the fermentative cycle and comes from a mother tun, with a solution of nutrient salts prepared in vessel 53 provided with a stirring means and pumped by one head of the two-head proportioning pump 36 through line 97 and with the recycled yeast through line 99. The stirring of the fermentation juice is carried out by circulating pump 39 and a jet mixer within the fermentation unit; the heat developed in fermentation unit 38 is eliminated by cooling the recycled rate flow through the plate exchanger 40.

The partially fermented juice passes by gravity through line 100 to second fermentation unit 41.

The stirring and cooling of the juice are carried out in the same way as in the first fermentation unit by pump 42 and plate exchanger 43.

The partially fermented juice passes by gravity through line 101 to third fermentation unit 44; the stirring and cooling are carried out in the same way as in the preceding fermentation units by pump 45 and plate exchanger 46.

In case of fermentation units of great capacity it is needed to provide a fourth fermentation unit in series and several fermentation lines as well.

During the fermentation the fermentable sugars are transformed by microorganisms into ethyl alcohol and carbon dioxide, the carbon dioxide being led through line 102 to the atmosphere or to a washing column for the recovery of alcohol.

The fermentation wine is extracted from the last fermentation unit 44 by circulating pump 45 through line 104, the level of the last fermentation unit as well as the level of the preceding units being controlled by controller LC6 acting on control valve 103.

The wine is led to centrifugal separator 47 through line 104. In the centrifugal separator the cells of the yeast are separated from the wine, thus providing wine free from cells and containing alcohol, which is led through line 106 to vessel 51, and a concentrated yeast suspension which is discharged into vessel 49.

Vessel 49 is provided with a stirrer to prevent yeast from being deposited.

Sulphuric acid is led to vessel 49 to prevent bacterial infection, said acid being pumped by one head of pump 13 through line 105. The acid is diluted in stationary mixer 48.

The suspension of yeast is recycled to first fermentation unit 38 through line 99 and proportioning pump 50.

Finally the wine is led to the distillation unit by pump 52 through line 108; the level of vessel 51 is maintained constant by controller LC7 acting on valve 107.

The operative conditions are listed in Table 1.

The starch is transformed in this phase in dextrines, i.e. polysaccharides having a lower molecular weight and being soluble in water.

The melted mass is led to acidification system 10 where sulphuric acid is added for the purpose of reducing pH to make the solution adapted to the saccharification enzyme (amidoglycosidase) and to coagulate the proteins existing under colloidal form; the pH is brought to values between 4 and 5.

The liquefied and acidified product is led to the separation system of the insoluble solids, mainly fibers, coagulated proteins and non-hydrolyzed starch.

The solid separation system consists, as mentioned above, of a screening stage provided with grid 14 of the stationary type with pressure nozzles arranged to supply pressurized

TABLE 1

| | Temperature °C. | Pressure mm Hg | pH | Alcohol concentration, % vol. | Microorganism Concentration grams of dry weight/l |
|---|---|---|---|---|---|
| Vessel | 50–60 | ATM | 5.5–6.5 | — | — |
| Tube 6 | 110–120 | 1070–1490 | — | — | — |
| Vessel 7 | 80–95 | 350–630 | — | — | — |
| Vessel 8 | 80–95 | ATM | — | — | — |
| Vessel 10 | 80–95 | ATM | — | — | — |
| Filter 16 | 60–70 | 150–230 | 4–5 | — | — |
| Saccharification unit 35 | 55–65 | ATM | — | — | 10–20 |
| Fermentation unit 38 | 30–33 | ATM | — | 5–6.5 | 10–20 |
| Fermentation unit 41 | 30–32 | ATM | — | 7–9 | 10–20 |
| Fermentation unit 44 | 30–32 | ATM | — | 8–10 | 10–20 |
| Vessel 49 | 25–35 | ATM | 2–3 | 2–3 | 130–150 |

The operation of the above described apparatus is now illustrated: the meal obtained from the milling of cereals with a grid of 1.5–2 mm and a middle size of 0.3–1 mm is led to suspension vessel 3 where it is diluted with recovery water at a solid concentration of 20–25% in weight and is heated at a temperature between 50° and 60° C.; the temperature of the suspension should not overcome 60° C. in order to prevent the starch from being gelatinized with a consequent abnormal increase in the viscosity.

Calcium chloride is added in a solution of 0.3–0.5 grams of Ca per kg of starch to make the action of the enzyme easier and the liquefaction enzyme (alpha-amylase) in the rate of 0.5–0.7 grams per kg of starch and soda for the correction of pH at 5.5–6.5.

The saccharification is carried out with a first cooking phase at 110°–120° C. for a time of the order of 5 minutes in tube 6 and then, after a cooling by self-evaporation of the suspension, in vessel 8 provided with a slow stirrer at 80°–95° C. for a time of the order of two hours.

The melted solution is recycled to expansion vessel 7 located above saccharification vessel 8 at a rate of 2–4 times as high as the rate of the hydrolyzed product in order to reduce the risk that expansion vessel 7 becomes dirty and to make the mixing of the suspension easier. An injection of alfa-amylase between cooking system 6 and liquefaction vessel 8 can be effected; in order to minimize the mixing problems in great capacity systems several liquefaction vessels may be provided in series.

liquid tangentially to a partially cylindrical surface of the grid 14 extending in an arc of approximately 120°. The grid is also supplied with the turbid filtrate obtained in the following filtration phase. The pressure of the nozzle can vary from 3 to 4 kg/cm² (relative pressure).

Two suspensions are obtained from screen 14: a limpid phase containing 1–1.5% in weight of insoluble solids having a lower size than the used screen, and a turbid phase containing the most of fibers and proteins as well as 5–8% in weight of insoluble solids.

The turbid suspension is led to the filtration system provided with filters 16 and 17 for the recovery of non-fermentable sugars and the thickening of the insoluble solids.

The first filter which is encountered is vacuum filter 16 of the horizontal band type. In this filter a filtration panel is obtained which is successively washed.

The quantity of washing warm water is of the order of 200–500% in weight of the dried solids in the filtration panel.

The absolute pressure in the filter is 150–230 mm Hg.

From vacuum filter 16 a panel containing 25 to 35% in weight of the solids is obtained.

In order to obtain a more dehydrated panel requiring less cost of drying, a mechanical pressing filter 17 is used which brings the solid content of the panel to values from 40 to 50% in weight.

The filtrates obtained in filters 16 and 17 are led to screen 14 to eliminate the suspended solids having larger dimensions and contained in a quantity of 1 to 2% in weight.

The filtration is fed by a suspension at 70°–85° C. and pH varying between 4 and 5.

The loss of soluble sugars in the solid separation unit is of the order of 2–3% of the total hydrolyzed sugar.

Such a quantity, however, is lost only as far as the alcohol fermentation is concerned as it remains in the panel and is used for the purpose of fodder.

The clarified must containing non-fermentable sugars is led to presaccharification tank 35 after cooling at 55°–65° C. and an addition of the amidoglycosidase enzyme at a rate of 1.5–2.5 grams per kg of starch.

The stirring is carried out by circulating the product externally at a rate of 5–10 times as high as the input rate.

The volume of the presaccharification tank is such as to assure a stay time of the order of 10 hours.

In case of great capacity systems several saccharification tanks will be provided in series to maximum the stirring efficiency.

The transformation of the starch into glucose is as a whole about 96% and is started in presaccharification tank 35 and completed in the continuous fermentation units 38.

The sugar substrate with a sugar concentration of 13% to 17% in weight is led to the first of the three or four fermentation units in series after cooling at 30°–35° C.

Sugars are metabolized into ethanol and carbon dioxide with a yield greater than 95% of the theoretical value (Pasteur) by performing the continuous fermentation under anaerobic condition and at atmospheric pressure and by using a culture of yeast of family *Saccharomyces cerevinae* with a concentration of 1 to 2% in weight of dry content and at a temperature between 30° and 35° C., and preferably at a lower temperature in the last fermentation units in order to mitigate the effect of the higher alcohol concentration, and with a pH between 4 and 5.

The temperature is maintained constant by outer circulation and cooling; the circulation at a rate of 5–10 times as high as the incoming rate allows the fermentation units to be stirred. Eventual calm zones within the fermentation units can give rise to sedimentation and overheating of the must with deactivation of the yeast and pollution of the must itself.

The recycle must and the nutrient salts are also led to the first fermentation unit 38 to maintain the cell concentration under optimum condition.

The fermentation wine with an alcohol concentration of 8% to 10% in volume is subjected to centrifugation in the centrifugal separator 47 for the separation of the limpid wine from the yeast cream.

The yeast cream from the centrifugal separator with a concentration of 14–18% in weight of dry content is collected in vessel 49 where it is diluted with water or light wine recovered from the carbon dioxide washing column and is acidified with sulphuric acid.

The reduction of pH to 2–3 is necessary to eliminate eventual pollution elements and to promote the lysis of the dead cells and to make the nutrient substances contained therein available.

The acidified suspension containing yeast in the rate of 130–150 g/l of dry content is recycled to the first fermentator.

The limpid wine is led to the following distillation unit for the recovery of ethanol.

It should ben noted that the first charge of yeast is prepared with common yeast without a pure culture in laboratory being needed.

The advantages of the described process and apparatus in terms of yield of ethanol and by-products as well as reduction of the energy needs of the process are shown in the following example.

EXAMPLE

In a typical case of continuous fermentation from milled maize in a pilot-plant for the treatment of about 250 kg/h or cereals, the maize has been milled with a grid of 2 mm, and the suspension of meal obtained by dilution with water in vessel 3 provided with a stirred had a solid concentration of 21.5% in weight at a temperature of 55° C.

The addition of Ca has been 0.47 grams per kg of starch and that of alpha amylase 0.56 grams per kg of starch.

The addition of NaOH was such as to bring the pH of the suspension to 6.

The cooking has been carried out at a temperature of 110° C. injector 5, and the self-evaporation in cyclone 7 at a pressure of 630 mm Hg has brought the liquefaction temperature in vessel 8 to 95° C.: in this phase 2% of starch has not been hydrolyzed.

The turbid liquefied mass is acidified in vessel 10 with a pH of 4.5.

The suspension is led to screen 14 at a temperature of 95° C. and after mixing with the turbid filtrate reaches the screen at 83° C.

A grid with 200 microns mesh has been used, thus providing a limpid solution with 1.3% of insoluble solid content and a turbid phase with 6,7% in weight of insoluble solids.

Filter 16 uses a quantity of washing water at 70° C. which is 2.5 times as high as the dry substance collected in the filtration panel.

The panel contains 30% in weight of solids and after squeezing in filter 17 the solid content is 45% in weight.

The collected filtrate led to screen 14 contains 1.5% in weight of insoluble solids.

The sugar loss in the filtration panel is 2.7% of the total hydrolyzed product.

The saccharification of the limpid must is carried out in tank 35 at 60° C. and the stirring is performed by recycling five times the incoming rate flow. The used quantity of enzyma (amidoglycosidase) is 1.9 grams per kg of starch.

The sugar concentration to continue the fermentation is maintained at 13.8% in weight and the temperature of fermentation is maintained at 32°–33° C. in first fermentation unit 38 and at 30°–31° C. in the other two fermentation units 41 and 44.

The yeast concentration is about 1.3% of the dry content in the three fermentation units. The outer circulation is about five times as high as the incoming rate flow.

The fermentation wine had a concentration of 8.5% in volume of alcohol.

The yeast cream obtained from centrifugal separator 47 at 16% in weight of the dry content is acidified at a pH of 2.5 before being recycled to the first fermentation unit.

The yield of ethanol was 60 liters per 100 kg of starch. The yield of fodder at 45% of the solid content was 0.4 kg per kg of maize.

The vapour consumption for the apparatus of this invention was 1.5 kg/l of the alcohol product.

The electric power consumption was 0.3 KWh per liter of the alcohol product.

A preferred embodiment of the invention has been thus described. It should be appreciated that the skilled in the art will be able to carry out many modifications. For example, it is possible to use mechanical mixing systems for the presaccharification tank to recover the vapour evaporated in the self-evaporation cyclone 7 and to compress it again for its re-utilization in cooking starch. The vacuum filter and the mechanical squeezing filter can be replaced by one unit performing the functions of both units.

All modifications and changes of this type are intended, however, as protected by the following claims as they do not depart from the scope of the invention and do achieve the same purposes thereof.

We claim:

1. A continuous cycle apparatus for the production of ethanol from an acidified hydrolyzed product of cereals obtained by an enzyme treatment of milled and cooked cereals, said apparatus comprising:

a stationary screen having a mesh size of 150–300 microns and having an inlet for receiving hydrolyzed product and recycled turbid filtrate, a first bottom outlet for limpid product, and a second bottom outlet for a turbid product;

a storing vessel for the turbid product having an inlet and an outlet, said inlet being connected to said second bottom outlet of said screen;

a stirrer in said storing vessel;

a horizontal band filter under vacuum having a first inlet connected to said storing vessel outlet, having a second inlet for receiving warm panel washing water, having a first outlet for a filtration panel, having a second outlet for a turbid filtrate and having a third outlet for the panel washing-water, said first band filter inlet being connected to said outlet of said storing vessel;

a mechanical squeezing filter coupled to said band filter first outlet for receiving the filtration panel for carrying out a hard dehydration of the filtration panel which is a by-product of the apparatus, said squeezing filter having an outlet for the panel and an outlet for a turbid filtrate;

filtrate receiving vessel means for receiving said turbid filtrate from said band filter second outlet through an inlet of said filtrate receiving vessel means, said filtrate receiving vessel means having an outlet coupled to said inlet of said stationary screen;

said filtrate receiving vessel means also receiving said turbid filtrate from said mechanical squeezing filter through an inlet of said filtrate receiving vessel means;

a limpid phase receiving vessel for receiving clarified hydrolyzed product from said first bottom outlet of said stationary screen through an inlet of said limpid phase receiving vessel, said limpid phase receiving vessel having an outlet;

a pre-saccharification tank coupled to said outlet of said limpid phase receiving vessel, said pre-saccharification tank having a bottom outlet;

a fermentation stage including yeast microorganisms coupled to said bottom outlet of said pre-saccharification tank and having an outlet for fermentation product;

a separator for separating the yeast microorganisms from the fermentation product, said separator having an inlet for receiving fermentation product from said fermentation stage and two outlets;

a yeast microorganisms treatment vessel having a stirrer therein and having two inlets and one outlet, one inlet being connected to one of said two outlets of said separator of yeast microorganisms, the other inlet being coupled to a source of sulfuric acid, and said outlet being coupled to said fermentation stage; and, a wine storing vessel having an inlet and an outlet, said inlet being connected to said other outlet of said separator of yeast microorganisms and said outlet being coupled to a distillation stage.

2. Apparatus as claimed in claim 1 wherein said fermentation stage includes three fermentation units.

3. Apparatus as claimed in claim 1 wherein said fermentation stage has a gas outlet conduit for gases outflowing from said fermentation stage coupled to a wine recovering and washing column.

4. The apparatus of claim 1 wherein said stationary screen comprises a grid with approximately 200 micron mesh.

5. The apparatus of claim 1 wherein said screen comprises a grid having a partially, generally cylindrical surface which extends through an arc of approximately 120° and wherein pressure nozzles are positioned adjacent said screen to supply pressurized liquid tangentially to said partially, generally cylindrical surface.

6. In an apparatus for processing cereals to obtain ethanol wherein a limpid phase of a slurry with water and hydrolyzed starch is supplied to a saccharification stage and an output of the saccharification stage is supplied to a fermentation stage to obtain a fermentation product from a fermentation product outlet of said fermentation stage and a wine from the fermentation product is supplied to a distillation stage to obtain ethanol, the improvement comprising:

a stationary screen with a mesh of between 150 and 300 microns which is positioned in the apparatus for receiving at an input of said screen, the slurry with water and hydrolyzed starch, said stationary screen having a turbid overscreen outlet and a limpid outlet containing a limpid solution having particles up to 150–300 microns and said limpid outlet being coupled to the saccharification stage so as to supply said limpid solution to the saccharification stage;

a vacuum band filter having an inlet coupled to the turbid overscreen outlet from said stationary screen, said vacuum band filter having a turbid filter outlet which is coupled back to said input to said stationary screen and having an outlet for a filtration panel; and a mechanical squeezing filter which is coupled to said filtration panel outlet from said vacuum band filter, which has a turbid filter outlet that is coupled to the inlet of said stationary screen and which has a dehydrated panel outlet.

7. The apparatus of claim 6 including:

a centrifuge device having an inlet coupled to the fermentation product outlet of the fermentation stage, having a limpid alcohol solution outlet which is coupled to the distillation stage and a yeast microorganism outlet, an acidifying vessel coupled to the microorganism outlet of said centrifuge device and having an outlet coupled back to an inlet to said fermentation stage.

8. The apparatus of claim 6 including means for cooking a slurry of water and milled cereals at a boiling temperature, means for stirring the cooked slurry for a period of time to allow the cooked slurry to cool to a temperature of between approximately 80° C. and 95° C., acidifying means for acidifying the cooked slurry to create a slurry of liquified and acidified product having a temperature of between approximately 70° C. and 85° C., means for supplying the cooked slurry to said acidifying means, and means for supplying said slurry of liquified and acidified product to said input of said stationary screen.

9. The apparatus of claim 6, wherein said screen comprises a grid having a partially, generally cylindrical surface which extends through an arc of approximately 120° and wherein pressure nozzles are positioned adjacent said screen to supply pressurized liquid tangentially to said partially, generally cylindrical surface.

* * * * *